(12) United States Patent
Obuki et al.

(10) Patent No.: US 8,178,840 B2
(45) Date of Patent: May 15, 2012

(54) SPECIMEN INSPECTION EQUIPMENT AND HOW TO MAKE THE ELECTRON BEAM ABSORBED CURRENT IMAGES

(75) Inventors: Tomoharu Obuki, Hitachinaka (JP); Hiroshi Toyama, Hachioji (JP); Yasuhiro Mitsui, Fuchu (JP); Munetoshi Fukui, Higashiyamato (JP); Yasuhiko Nara, Hitachinaka (JP); Tohru Ando, Tokyo (JP); Katsuo Ooki, Kasama (JP); Tsutomu Saito, Hitachinaka (JP); Masaaki Komori, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 57 days.

(21) Appl. No.: 12/691,331

(22) Filed: Jan. 21, 2010

(65) Prior Publication Data
US 2010/0116986 A1 May 13, 2010

Related U.S. Application Data

(63) Continuation of application No. 12/038,079, filed on Feb. 27, 2008, now Pat. No. 7,663,104.

(30) Foreign Application Priority Data

Feb. 28, 2007 (JP) .................................. 2007-048369

(51) Int. Cl.
*G01N 23/225* (2006.01)
*H01J 37/28* (2006.01)
(52) U.S. Cl. ........ 250/310; 250/311; 250/306; 250/307; 324/750.01; 324/750.24; 324/754.01; 324/754.03
(58) Field of Classification Search .......... 250/306–311, 250/462.2, 462.3, 492.2, 492.3; 324/750.01, 324/750.24, 754.01, 754.03, 754.22
See application file for complete search history.

(56) References Cited

U.S. PATENT DOCUMENTS

| | | | | |
|---|---|---|---|---|
| 6,653,629 B2* | 11/2003 | Tanaka et al. | ................. | 250/306 |
| 7,663,104 B2* | 2/2010 | Obuki et al. | ................. | 250/311 |
| 2002/0008201 A1* | 1/2002 | Tanaka et al. | ................. | 250/310 |
| 2008/0203297 A1* | 8/2008 | Obuki et al. | ................. | 250/307 |

FOREIGN PATENT DOCUMENTS

| | | |
|---|---|---|
| JP | 5-203709 A | 8/1993 |
| JP | 2002-343843 A | 11/2002 |
| JP | 2002-368049 A | 12/2002 |
| JP | 2003-185605 A | 7/2003 |
| JP | 2004-296771 A | 10/2004 |

* cited by examiner

*Primary Examiner* — Bernard E Souw
(74) *Attorney, Agent, or Firm* — Crowell & Moring LLP

(57) ABSTRACT

An object of the present invention is to obtain a clear absorbed current image without involving the difference in gain of amplifier between inputs, from absorbed currents detected by using a plurality of probes and to improve measurement efficiency.

In the present invention, a plurality of probes are brought in contact with a specimen. While irradiating the specimen with an electron beam, currents flowing in the probes are measured. Signals from at least two probes are input to a differential amplifier. An output of the differential amplifier is amplified. On the basis of the amplified output and scanning information of the electron beam, an absorbed current image is generated. According to the invention, a clear absorbed current image can be obtained without involving the difference in gain of amplifier between inputs. Thus, measurement efficiency in a failure analysis of a semiconductor device can be improved.

5 Claims, 2 Drawing Sheets

SPECIMEN INSPECTION EQUIPMENT AND HOW TO MAKE THE ELECTRON BEAM ABSORBED CURRENT IMAGES

CROSS REFERENCE OF RELATED APPLICATIONS

This application is a continuation of U.S. application Ser. No. 12/038,079 filed Feb. 27, 2008.

CLAIM OF PRIORITY

The present application claim priority from Japanese application serial No. 2007-048369, filed on Feb. 28, 2007, the content of which is hereby incorporated by reference into this application.

BACKGROUND OF THE INVENTION

1. Field of the Invention

The present invention relates to specimen inspection equipment for analyzing a semiconductor device or the like and how to make electron beam absorbed current images using the same. For example, the invention relates to the technique of identifying a location of electrical failure in a wiring pattern on a semiconductor device or the like.

2. Description of the Related Art

In a semiconductor device on whose semiconductor surface a circuit is formed, it is becoming more difficult to identify a failure location as the device is becoming finer, so that it takes long time to perform the failure analysis. For the analysis, analysis equipment such as OBIRCH (Optical Beam Induced Resistance Change) equipment, an EB tester, or the like has been used at present.

As a failure analysis on a wiring pattern in the failure analysis on the semiconductor device, in recent years, attention is being paid to the technique of irradiating the surface of the semiconductor device with an electron beam, analyzing current absorbed by the wiring pattern or a secondary signal emitted from the semiconductor device, and forming an image from the current/signal.

Japanese Patent Application Laid-Open No. 2002-368049 discloses the technique of identifying a failure location in a semiconductor device by bringing probes into contact with both ends or one end of a pattern, scanning the pattern on the semiconductor device with an electron beam, measuring current flowing in the probes, and forming an image.

Japanese Patent Application Laid-Open No. 2004-296771 discloses the technique of amplifying signals from a plurality of probes, obtaining the difference between the signals, performing a scanning with the differential amplification signals, and displaying an image, and the technique of modulating an electron beam, performing a scanning with the modulated electron beam, and displaying an image.

As described in the conventional techniques, at the time of measuring current outputted from a probe, when one probe is connected to a current amplifier, another probe is grounded, and signals from the probes are measured by the current amplifier, the situation is as follows.

When probes are in contact with both ends of a wiring pattern and a semiconductor device is irradiated/scanned with an electron beam in that state, some of current supplied to the wiring pattern (absorbed current) flows from the point where the electron beam strikes to the ground, and the other flows toward the current amplifier. In this case, the original resistance of the wiring pattern is divided between portions each from the point where the electron beam strikes to the contact point of different one of said probes. The absorbed current supplied from the electron beam to the wiring pattern is bifurcated according to the divided resistance values, and the resultant currents each are passed to either the ground or the current amplifier. With the measuring method, when a failure exists in the wiring pattern, a difference due to the abnormal resistance value can be observed, so that a location of the failure can be identified. However, when the resistance of the pattern is smaller than input impedance of the current amplifier, the absorbed current flows to the ground more than to the current amplifier. When the difference between the resistance of the pattern and input impedance of the current amplifier is large, the difference between absorbed currents each flowing in either the ground or the current amplifier increases, and flow of the absorbed current to the current amplifier is suppressed. Consequently, a wiring pattern having a small resistance value cannot be measured, and a failure location cannot be identified.

Similarly, in the case of the measurement using two probes, inputs of the differential amplifier are connected to the outputs of each amplifier in the conventional configuration. Currents outputted from the probes are amplified by the different amplifiers and, after that, the amplified currents are supplied to the differential amplifier. In this case, the signals which are amplified by the different gain according to the individual difference among the amplifiers connected to the input of the differential amplifier are input to the differential amplifier. As a result, there is a case such that the differential signal between the signals obtained by amplifying the currents input from the probes at their respective different gains is amplified by the differential amplifier, and that a value different from the actual current is measured.

In the case where one of input signals to the differential amplifier is amplified extremely larger than the other signal, the output goes off the scale to the positive or negative side. To avoid such a state of things, the amplifiers have to be adjusted to have the same gain and the same offset. Consequently, measurement itself is also complicated.

Further, since the differential amplifier is used, when the probes come into contact with both ends of a wiring pattern, a loop is formed between input terminals of the differential amplifier through a connection cable from the probes to the input terminals. As the loop is influenced by the magnetic field, in the case where a magnetic shield is not provided, currents determined by both an induced electromotive force generated by the magnetic field and the impedance of the wiring pattern may be directly superimposed as noise upon the signals of the input current from the probes.

SUMMARY OF THE INVENTION

An object of the present invention is to obtain a clear absorbed current image without involving the different gain between inputs, from absorbed currents detected by using a plurality of probes and to improve measurement efficiency.

In the present invention, a plurality of probes are kept in contact with a specimen. While irradiating the specimen with an electron beam, currents flowing in the probes are measured. Signals from at least two probes are input to a differential amplifier, and an output of the differential amplifier is amplified. On the basis of the amplified output and scanning information of the electron beam, an absorbed current image is generated.

In the present invention, a plurality of probes are kept in contact with a specimen. While irradiating the specimen with an electron beam, currents flowing in the probes are measured. A signal depending on current flowing in one probe is input to the input side of an amplifier, and a signal depending on current flowing in another probe is input to the GND of the amplifier. On the basis of the output from the amplifier and scanning information of the electron beam, an absorbed current image is generated.

In the present invention, a specimen is irradiated with an electron beam in a state where probes are apart from the specimen and noise information is generated. The specimen is irradiated with an electron beam in a state where the probes are in contact with the specimen and absorbed current information is generated. On the basis of the absorbed current information and the noise information, an absorbed current image is generated.

According to the invention, a clear absorbed current image can be obtained without involving the different gain between inputs. Thus, measurement efficiency in a failure analysis of a semiconductor device can be improved.

DESCRIPTION OF THE PREFERRED EMBODIMENTS

Embodiments of the present invention will be described hereinbelow with reference to the appended drawings.

First Embodiment

Figure 1:
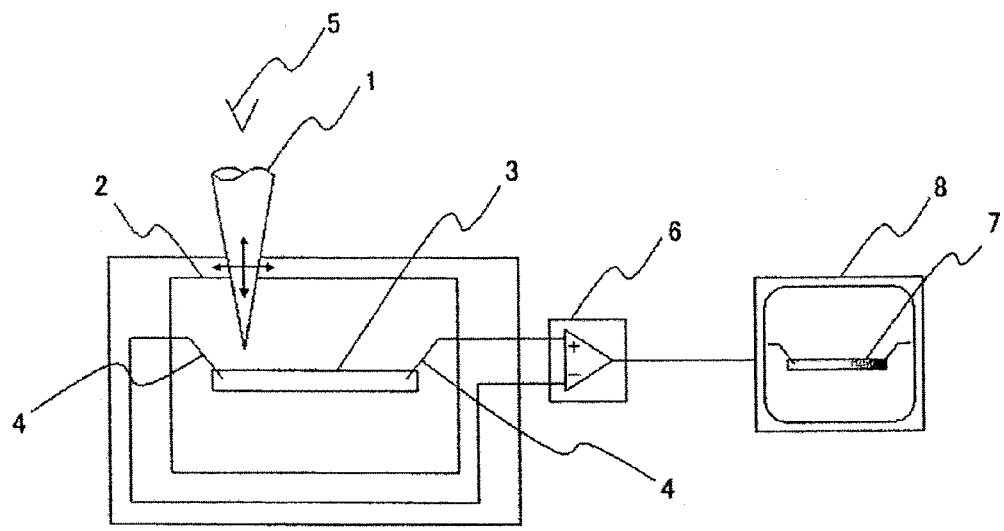
FIG. 1 is a diagram showing a schematic configuration of specimen inspection equipment according to an embodiment of the present invention.

FIG. 1 is a diagram showing a schematic configuration of specimen inspection equipment according to an embodiment of the present invention.

Primary electrons 1 are emitted to a specimen 2. A pattern 3 is formed on the surface of the specimen 2, and probes 4 are brought into contact with both ends of the pattern 3 or pads. In this state, the surface of the specimen 2 including the pattern 3 is scanned with the primary electrons 1 from an electronic source 5. Electrons entering the pattern 3 among the emitted primary electrons 1 are detected as currents by the probes 4, and the detected current signals are supplied to a differential amplifier 6 and amplified. The differential amplifier 6 generates a differential signal from the input signals and outputs it. The differential signal is displayed as an absorbed current image 7 on a monitor 8, in synchronization with the scanning of the primary electrons 1.

The current passed through the pattern 3 and detected by the probe 4, which has been bifurcated according to the resistance values of portions of the pattern 3, each portion being from the point where the primary electrons 1 strike to different one of the probes 4, is input to the positive input or the negative input of the differential amplifier 6. As a result, according to a change in the resistance value between the contacts of the probes 4 in the pattern 3, contrast occurs in the absorbed current image 7. Since the resistance value is not uniform in a failure part in the pattern 3, the contrast is displayed in a manner different from the other normal part. Consequently, the different state, that is, the failure location in the pattern 3 can be easily determined in the absorbed current image 7.

Figure 2:
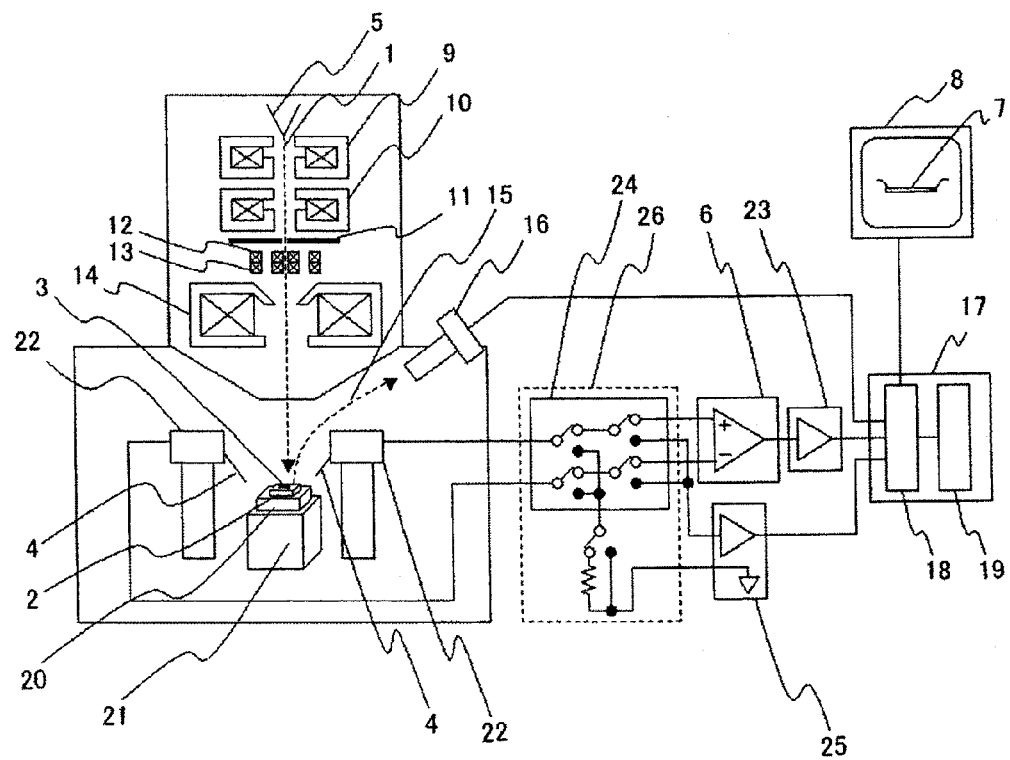
FIG. 2 is a diagram showing the configuration of the specimen inspection equipment of the embodiment including the configuration illustrated in FIG. 1.

FIG. 2 is a diagram showing the configuration of the specimen inspection equipment of the embodiment including the configuration illustrated in FIG. 1.

In FIG. 2, the specimen inspection equipment has electron optics capable of emitting an electron beam. That is, the primary electrons 1 emitted from the electronic source 5 pass through condenser lenses 9 and 10, an aperture 11, a scan deflector 12, an image shift deflector 13, and an objective lens 14 and are irradiated with to the specimen 2. The surface of the specimen 2 is scanned with the primary electrons 1 by the scan deflector 12 and the like.

A secondary electron beam 15 is emitted from the specimen 2 irradiated with the primary electrons 1 and is detected by a secondary electron detector 16.

The secondary electron detector 16 as a detector capable of detecting secondary electrons generated from the specimen is controlled by an SEM control unit 17. The SEM control unit 17 has a video board 18 and a memory 19. The signal input from the secondary electron detector 16 is converted to a digital signal by the video board 18, and an image is displayed on the monitor 8 in synchronization with the scanning using the primary electrons 1. Since the image is displayed on the monitor 8 in synchronization with the primary electrons 1 used for the scanning, the secondary electron beam 15 is displayed as an SEM image. The signal and the SEM image are recorded in the memory 19. The whole specimen inspection equipment is also controlled by the SEM control unit 17.

The specimen 2 is fixedly held by a specimen holder 20 and can be moved in three axis directions of X, Y, and Z axis by a specimen stage 21 on which the specimen can be mounted. The probe 4 which can be brought into contact with the specimen can be moved in three axis directions of X, Y, and Z by a probe stage 22 similar to the specimen stage 21.

Each of the specimen stage 21 and the probe stage 22 is moved/controlled in the three axis directions of X, Y, and Z to make the probe 4 come into contact with the surface of the specimen 2.

The probes 4 are brought in contact with one end or both ends of a wiring pattern formed on the surface of the specimen 2. In this state, the surface of the specimen 2 including the pattern 3 is scanned with the primary electrons 1 emitted from the electronic source 5. Electrons entering the pattern 3 among the emitted primary electrons 1 are detected as current by the probe 4. The current flowing in the probe is measured by a measuring instrument. The current flowing in the pattern 3 and being detected by the probe 4 has been bifurcated according to the resistance values of portions of the pattern 3, each portion being from the point where the primary electrons 1 strike to different one of the probes 4, and the resultant signals are input to the differential amplifier 6. The differential amplifier 6 to which the signals from the measuring instrument are input generates a differential signal from the input signals and outputs the generated differential signal. The differential signal output from the differential amplifier 6 is amplified by an amplifier 23 at gain necessary to display the absorbed current image 7 based on the absorbed currents from the probes 4. In synchronization with the scan using the primary electrons 1, the absorbed current image 7 is displayed on the monitor 8 as an imaging device for outputting an absorbed current image on the basis of both the signal from the differential amplifier and a signal depending on the scan of the electron optics.

As described above, the SEM control unit 17 has the video board 18 and the memory 19. The signal input from the probe 4 is converted to a digital signal by the video board 18 and displayed on the monitor 8 in synchronization with the scan of the primary electrons 1. As a result, a distribution of signals (absorbed current signals) obtained from the currents (absorbed currents) input from the probes can be displayed as an image (which will be called the absorbed current image 7). The signals and the absorbed current image 7 are recorded in the memory 19.

Consequently, according to a change in the resistance value between the contacts of the probes 4 in the pattern 3, contrast is generated in the absorbed current image 7. Since the resistance value is not uniform in the failure part in the pattern 3, the contrast is displayed in a manner different from the other normal part. Therefore, the different state, that is, the failure location in the pattern 3 can be easily determined in the absorbed current image 7.

The SEM control unit 17 has the function of switching a signal input system for displaying an image between the secondary electron detector 16 and the differential amplifier 6. At the time of displaying the absorbed current image 7 on the basis of the current from the probe 4, the SEM control unit 17 switches the probe 4 to the differential amplifier 6 side.

By displaying the signal for generating the input absorbed current image 7 on the monitor 8 in synchronization with the scanning using the primary electrons 1, the absorbed current image 7 is displayed.

A switch 24 is mounted at the front of the differential amplifier 6. While the specimen 2 is irradiated with the primary electrons 1, the probe 4 is also irradiated with the primary electrons 1, so that there is the possibility that the probe 4 is charged. The charged probe 4 is discharged when it approaches the specimen 2. The probe 4 has a diameter of several hundreds of nm and is very thin, so that the probe 4 may be damaged by the discharge. Many of the specimens 2 are not resistive to static electricity and may be damaged by discharge. That is, when the charged probe 4 is brought near to the specimen 2, the probe 4 and the specimen 2 may be damaged. The switch 24 is to be grounded until the probe 4 is brought into contact with the specimen 2. After the probe 4 comes into contact with the specimen 2, the switch 24 is switched to the differential amplifier 6 side. In such a manner, the probe 4 can be brought in contact with the specimen 2 without being charged.

The switch 24 can be selectively connected to the differential amplifier 6 and a current amplifier 25.

In the case of keeping probes in contact with both ends of the pattern 3 and conducting measurement using the current amplifier 25, in the switch 24, one of the probes in contact with both ends of the pattern 3 is connected to the current amplifier 25 and the other probe is connected to the GND of the current amplifier via a resistor. The resistor is selectable and can be switched according to the resistance value of the specimen.

By bringing the probes 4 into contact with both ends of the pattern 3 on the surface of the specimen 2, a circuit forming a loop connecting the inputs of the differential amplifier 6 is generated. In the case where an external magnetic field is generated around the circuit, an induced electromotive force is generated by the loop involving the wiring pattern and the like connecting the inputs of the differential amplifier 6. On the basis of the impedance of the loop, currents flow by the induced electromotive force and are supplied via inputs of the differential amplifier 6. The currents are superimposed as noise upon the absorbed current image 7. In the semiconductor test equipment, the portion from the probes 4 to the inputs of the differential amplifier 6 is covered with a shield 26. By the shield 26, the influence of the magnetic field on the loop is largely reduced and the induced electromotive force is reduced. Thus, the noise superimposed is largely reduced.

In the present embodiment, because of receiving signals flowing in the probes directly by the differential amplifier, no difference occurs in signal gain between the input systems. By amplifying the difference between the input signals themselves, an output having no bias in amplification/output can be obtained. Thus, the image quality improves dramatically. The influence on input signals can be decreased as compared with the conventional technique, so that an absorbed current image formed by an input signal smaller than that in the conventional technique can be observed. As a result, an absorbed current image of a to-be-measured specimen with a resistance value smaller than that in the conventional technique can be also observed. As for the adjustment of amplifier, since the first amplifier is differential amplifier and the influence of the amplifier on an offset is dominant, the offset adjustment on each of the input systems is unnecessary and only the adjustment in a lump is needed. Therefore, only the adjustment for the differential amplifier is all that is needed. Complication of the device adjustment in observation of the absorbed current image can be lessened, and the convenience improves dramatically.

While connecting one of probes to the ground via the resistor, and connecting another probe to the current amplifier, the input signals from the probes are displayed as an image in synchronization with the scanning means. Thus, the currents having flowed in from the probes flow not only to the ground side but also to the current amplifier side. Consequently, by selecting the resistance value to the ground, the range of resistance values of specimens which can be measured is widened, and a specimen having a resistance value smaller than that in the conventional technique can be measured.

Second Embodiment

Figure 3:
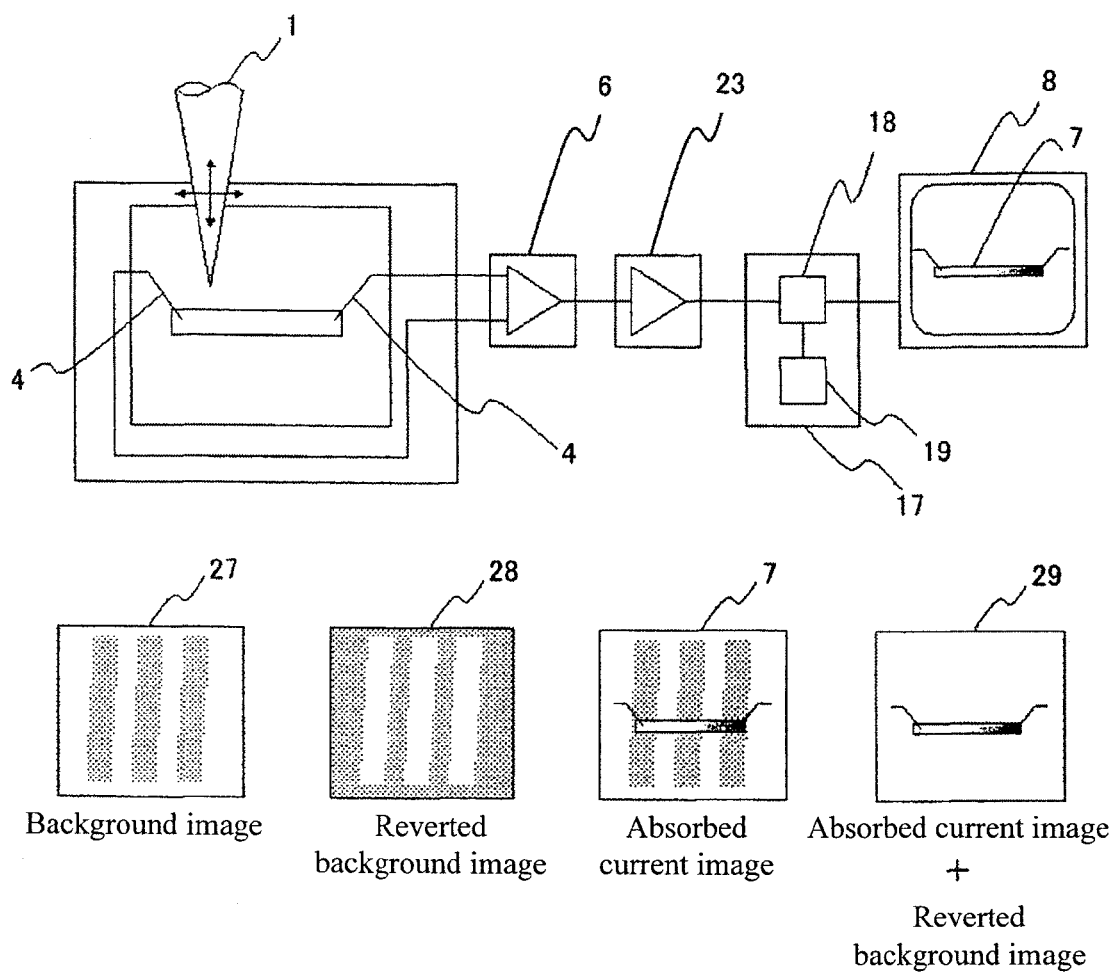
FIG. 3 shows an example of a method of reducing the influence of agitation noise on an absorbed current image 7.

In the detection system of the first embodiment, the gain has to be high, so that the configuration is sensitive to agitation noise. FIG. 3 shows an embodiment reducing the influence of the agitation noise on the absorbed current image 7. Only the points different from the first embodiment will be described below.

Before the probes 4 are made into contact with the specimen 2, the primary electrons 1 are emitted once, and an absorbed current image formed by signals from the probes 4 is measured. The signal input from the probe 4 is converted to a digital signal by the video board 18 and the digital signal is recorded in the memory 19. The signal is used as a background signal, and an image formed by the signal is shown as a background image 27. A signal is generated by inverting the polarity of signal data of the background signal once recorded in the memory 19 by the SEM control unit 17, and the generated signal is recorded in the memory 19. The signal is set as a reverted background signal, and an image formed by the reverted background signal is shown as a reverted background image 28. The signal consists of only the signal component of the agitation noise which does not depend on the sample, from the periphery.

Next, the probes 4 are brought into contact with the specimen 2, the absorbed current at that time is measured, input signals from the probes 4 at that time are similarly converted to digital signals by the video board 18, and the digital signals are recorded in the memory 19. The signal is set as an absorption current signal, and an image formed by the signal is shown as the absorbed current image 7. On the absorbed current signal, the agitation noise obtained before is also superimposed. The reverted background signal recorded before is read from the memory 19 and added to the absorbed current signal. The resultant signal is displayed on the monitor 8 in synchronization with the scanning using the primary electrons 1 (absorbed current image+reverted background image 29). As a result, the background corresponding to an agitation noise is cancelled out, and the agitation noise can be largely reduced.

In the embodiment, by subtracting the background noise from the absorbed current image, deterioration in the image quality caused by the noise can be largely reduced.

What is claimed is:

1. A specimen inspection equipment comprising:
  a specimen stage on which a specimen can be mounted;
  a plurality of probes;
  a probe stage which moves the probes so as to be brought into contact with the specimen;
  an electron optics which emits an electron beam onto a pattern of the specimen which is brought into contact with the probes; and
  an imaging device which outputs an absorbed current image on the basis of current flowing in the probes.

2. The specimen inspection equipment according to claim 1, further comprising:
  a differential amplifier which outputs a differential signal between the plurality of probes,
  wherein the imaging device outputs the absorbed current image on the basis of an output of the differential amplifier.

3. The specimen inspection equipment according to claim 1, further comprising:
  a detector which detects an electron generated based on the emission of the electron beam; and
  a controller which switches between an output of the detector and an output of the differential amplifier,
  wherein the imaging device switches a display image between the absorbed current image and a secondary electron image in response to the switching operation by the controller.

4. A specimen inspection equipment comprising;
  a specimen stage on which a specimen can be mounted;
  a plurality of probes;
  a probe stage which moves the probes so as to be brought into contact with the specimen;
  an electron optics which emits an electron beam onto a pattern of the specimen which is brought into contact with the probes;
  a detector which detects an electron generated based on the emission of the electron beam; and
  an imaging device which displays a sum signal of an absorbed current image signal based on current flowing in the probes and a reverted background image signal based on an output of the detector.

5. The specimen inspection equipment according to claim 4, further comprising:
  a differential amplifier which outputs a differential signal between the plurality of probes; and
  a memory Which stores an output of the differential amplifier and the output of the detector.

* * * * *